United States Patent [19]

Rentél et al.

[11] Patent Number: 4,563,533
[45] Date of Patent: Jan. 7, 1986

[54] PROCESS FOR THE PREPARATION OF HALOGEN-SUBSTITUTED 2-AMINOBENZOTHIAZOLES

[75] Inventors: Heinz Rentél, Kronberg; Theodor Papenfuhs, Frankfurt am Main, both of Fed. Rep. of Germany

[73] Assignee: Hoechst Aktiengesellschaft, Fed. Rep. of Germany

[21] Appl. No.: 526,523

[22] Filed: Aug. 25, 1983

[30] Foreign Application Priority Data

Aug. 27, 1982 [DE] Fed. Rep. of Germany ....... 3231885

[51] Int. Cl.$^4$ ............................................. C07D 277/82
[52] U.S. Cl. .................................................... 548/164
[58] Field of Search ........................................ 548/164

[56] References Cited

U.S. PATENT DOCUMENTS 1,910,489  5/1933  Lubs .................................... 548/164

Primary Examiner—Robert Gerstl
Attorney, Agent, or Firm—Connolly and Hutz

[57] ABSTRACT

A process for the preparation of halogen-substituted 2-aminobenzothiazoles of the formula (1)

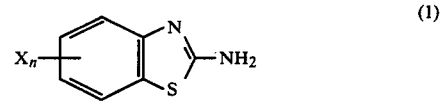

starting from halogen-substituted phenylthioureas of the formula (2)

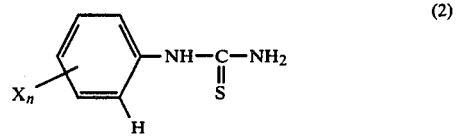

by cyclization reaction with sulfuryl chloride in an inert solvent, wherein X is chlorine and/or bromine and n is an integer of from 1 to 4, and the cyclization reaction is carried out in the presence of an alkali metal or alkaline earth metal oxide, hydroxide or carbonate.

9 Claims, No Drawings

PROCESS FOR THE PREPARATION OF HALOGEN-SUBSTITUTED 2-AMINOBENZOTHIAZOLES

Halogen-substituted 2-aminobenzothiazoles are important intermediates for the manufacture of dyestuffs (see for example German Auslegeschrift No. 1,907,606, U.S. Pat. No. 3,502,645), and starting products for biologically active substances, for example of 2-chlorobenzothiazoles halogen-substituted in the benzene nucleus (see for example Czech Pat. No. 164,118 (C.A. 87 (1977) 53258t), British Pat. No. 966,496).

For the synthesis of 2-aminobenzothiazoles, practically two alternatives are known:

(1) Alkaline cyclization of o-thiocyanogen anilines (see for example German Pat. No. 491,223 (Friedl. 16 2566/68), J. Am. Chem. Soc. 58 (1936) 1364/66, French Pat. No. 1,502,178). This synthesis method requires the technically and above all ecologically problematic preparation, at least intermediately, of dithiocyanogen (from alkali metal rhodanide and halogen), gives pure products in rarest cases only and necessitates a high expenditure for the removal of off-gas (HSCN) and waste water (bromide).

(2) Oxidative cyclization of the corresponding arylthioureas. Halogens (chlorine, bromine) and compounds splitting off halogen, especially sulfur halogen compounds, for example disulfur dichloride, thionyl chloride, sulfuryl chloride, have been proposed as oxidative cyclization agents (see for example R. C. Elderfield, Heterocyclic Compounds, Vol. 5, New York/London 1957, pp. 581/82). In Published European Patent application No. 0,003,141, the cyclization of arylthioureas with thionyl chloride to give 2-aminoarylenothiazoles, for example halogen-substituted 2-aminobenzothiazoles, is described. However, in this syntheses, considerable amounts of elementary sulfur are obtained the removal of which necessitates a certain expenditure.

This disadvantage is avoided by using sulfuryl chloride. In U.S. Pat. No. 2,033,949, the synthesis of fluorine-substituted 2-aminobenzothiazoles from the corresponding phenylthioureas by cyclization reaction with sulfuryl chloride in a suitable inert solvent, for example chlorobenzene, is described. Under the reaction conditions as described, the synthesis of the analogous chlorine and bromine compounds however gives absolutely insufficient yields.

It was therefore the object of the invention to provide a process for the preparation of chlorine-substituted or bromine-substituted 2-aminobenzothiazoles which ensures their obtention with high yields and a high purity degree. It has been found that this object is achieved by carrying out the cyclization with sulfuryl chloride in an inert solvent in the presence of an alkali metal or alkaline earth metal oxide, hydroxide or carbonate.

There has been found a process for the preparation of halogen-substituted 2-aminobenzothiazoles of the formula (1)

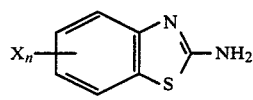

starting from halogen-substituted phenylthioureas of the formula (2)

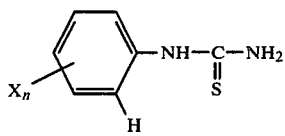

by cyclization reaction with sulfuryl chloride in an inert solvent, wherein X is chlorine and/or bromine and n is an integer of from 1 to 4, and the cyclization reaction is carried out in the presence of an alkali metal or alkaline earth metal oxide, hydroxide or carbonate.

Generally, small amounts of water do not disturb the reaction; in some cases a small amount of about 0.5 to 10 weight %, relative to the starting phenylthiourea, surprisingly has even a positive effect on the yield and quality of the halo-2-aminobenzothiazoles obtained. A water amount of up to 25 weight % can be tolerated and does not adversely affect the cyclization reaction and its speed. Larger amounts of water however retard the reaction and/or result in increased consumption of sulfuryl chloride, and should therefore be avoided.

The reaction temperature is advantageously in the range of from about 30° to about 80° C., preferably about 45° to about 65° C.

Suitable solvents are those in which sulfuryl chloride is dissolved but does not react therewith. Preferred examples are alkyl-substituted aromatic substances such as toluene and the xylenes, haloaliphatic substances such as ethylene chloride, trichloroethane and trichloroethylene, especially haloaromatic substances such as chlorobenzene, bromobenzene, the di- and trichlorobenzenes and chlorotoluenes. Mixtures of the cited solvents may furthermore be used.

The amount of solvent used is not critical; however, it must be proportioned such that the reaction mixture can be well stirred in any phase of the reaction in order to ensure the gaseous reaction products HCl and $SO_2$ to be driven off. These products are advantageously reacted with water and subsequently alkaline lyes in two-step or multiple-step scrubbers to yield hydrochloric acid solutions and alkali hydrogen sulfite solutions which can be reused.

Examples of alkali or alkaline earth metal compounds to be used as acid-binding agents are preferably alkali or alkaline earth metal carbonates such as sodium, potassium, magnesium, calcium and barium carbonate, alkaline earth metal hydroxides such as magnesium, calcium and barium hydroxide, especially alkaline earth metal oxides such as magnesium, calcium and barium oxide. Mixtures of the cited alakali and alkaline earth compounds may also be used. Especially preferred is magnesium oxide.

Generally, one equivalent of acid-binding agent is used per mol of arylthiourea. A small excess is not critically a high excess, for example 2 or more equivalents, retards the cyclization to such an extent that complete conversion becomes impossible within an economically interesting reaction time. When using on the other hand less than 1 equivalent of acid-binding agent, undesirable by-products are formed, for example halogen-substituted phenylureas, elementary sulfur and/or halobenzothiazolyl-halophenylguanidines, which may become main products or even the sole reaction product in case of the acid-binding agent being absent.

The halogen-substituted phenylthioureas of the formula (2) are easily obtainable by reaction of the corresponding halogen-substituted arylamine salts with rhodanides, especially according to the process of European Patent application No. 0,005,276, because it yields the thioureas in the form of coarse crystals binding a small amount of water only, which generally can be used directly in moist state for the process of the invention, so that an expensive drying of the starting material can be renounced.

In many cases, isolation of the halogen-substituted phenylthioureas can be entirely avoided, that is, when their synthesis is carried out in the solvent suitable for the cyclization reaction according to the invention by reaction of, for example, halogenated phenylamine sulfate (in situ produced from the free base and concentrated sulfuric acid in the solvent) with alkali metal rhodanide. In this one-pot reaction, the suspension of the halogenated phenylthiourea which has formed is directly reacted with sulfuryl chloride in the presence of the alkali or alkaline earth metal compounds applied in accordance with the invention.

The amount of sulfuryl chloride required for a quantitative cyclization is at least 1 mol of SO₂Cl₂ per mol of phenylthiourea. An excess of from 10 to 100%, preferably 30 to 70%, has proved in the practice to be favorable, that is, from 1.1 to 2, preferably 1.3 to 1.7, mol of SO₂Cl₂ per mol of phenylthiourea.

The process of the invention is carried out as follows: the acid-binding agent and optionally water are added to the stirred solvent suspension of the halogenated phenylthiourea to be cyclized, the batch is heated to reaction temperature, and the necessary amount of sulfuryl chloride is added dropwise within 1 to 5 hours depending on the reaction heat or gas amounts set free. For work-up, either the halogenated 2-aminobenzothiazolium salt precipitated during the cyclization, for example the chloride and/or sulfate, can be separated from the solvent by filtration and, optionally after drying, converted to the free halogenated 2-aminobenzothiazole by treatment with aqueous alkali lye (advantageous in the case of some compounds because of the purification effect observed), or the reaction mixture, optionally after previous neutralization with ammonia or other alkalis, can be liberated from the solvent by steam distillation, and the halogenated 2-aminobenzothiazole can be isolated in the form of salt or free base by filtration from the resulting aqueous suspension, optionally after previous cooling.

The process of the invention allows furthermore the synthesis of halogen-substituted 2-amino-arylenothiazoles having more than one benzene nucleus, for example halogen-substituted 2-amino-naphthylenothiazoles of the formulae (1a) or (1b)

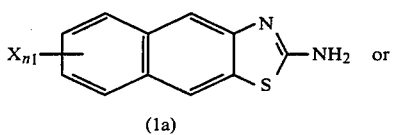
(1a)

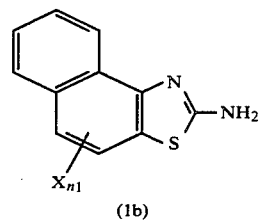
(1b)

starting from halogen-substituted napthylthioureas of the formulae (2a) or (2b)

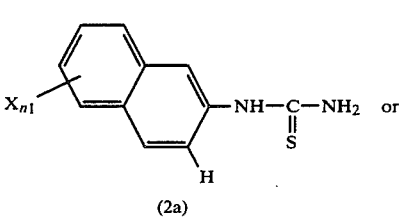
(2a)

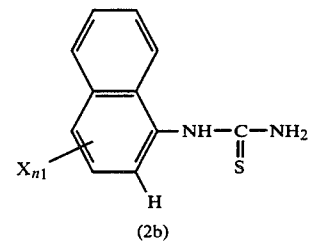
(2b)

in which formula n₁ is an integer of from 1 to 6.

The following examples illustrate the invention without limiting it in its scope. Parts and percentages are by weight unless otherwise stated.

EXAMPLE 1

186.5 Parts of 4-chlorophenylthiourea and 20 parts of magnesium oxide were introduced with stirring into 800 parts of chlorobenzene, and the suspension was heated to about 50° C. At this temperature, a mixture of 222.7 parts of sulfuryl chloride and 150 parts of chlorobenzene were added dropwise within about 2 hours ½. Subsequently, stirring was continued for about 3 hours at 50°–55° C. until the development of gas had ceased. The escaping gases (HCl and SO₂) were absorbed in two-step absorption plant containing water and sodium hydroxide solution, respectively, and thus converted to hydrochloric acid and sodium bisulfite, respectively. Cyclization being complete, 200 parts of water were added dropwise, and the pH was adjusted to 8–8.5 by means of about 200 parts of 33% ammonia. The chlorobenzene was then distilled off by means of steam, the 2-amino-6-chlorobenzothiazole was suction-filtered at room temperature, washed with water and dried in a drying cabinet with air circulation at about 80° C. Yield: 171.3 parts=92.8% of th., mp. 188°–195° C.

EXAMPLE 2

186.5 Parts of 4-chlorophenylthiourea and 50 parts of calcium carbonate were introduced with stirring into 900 parts of o-dichlorobenzene, and 223 parts of sulfuryl chloride were added within 3 hours at a temperature of 45°–50° C. to the suspension. Stirring was continued thereafter for 3 hours at 50°–55° C. until the development of gas had ceased. The product was suction-filtered via a glass frit, washed first with chlorobenzene and then with petroleum ether (boiling range 80°–100° C.), and dried.

The crude product obtained was stirred in 600 parts of 96% sulfuric acid. The suspension obtained was poured into 3,000 parts of water, the batch was heated to about 90° C., 30 parts of active charcoal were added, and the batch was filtered. The clarified filtrate was adjusted to pH 10–11 by means of 25% sodium hydroxide solution (concentrated ammonia may also be used), the precipitate was suction-filtered at room temperature, washed to neutral and dried. Yield: 194 parts of 2-amino-6-chlorobenzothiazole=87.5% of th.

EXAMPLE 3

101.6 Parts of 4-chlorophenylthiourea (91.7% strength, moist) and 35 parts of barium oxide were introduced with stirring into 400 parts of chlorobenzene. At a temperature of 52°–55° C., a mixture of 116.9 parts of sulfuryl chloride and 70.0 parts of chlorobenzene was added dropwise within about 3 hours. Stirring was continued for about 5 hours at this temperature until the development of gas had ceased. The cyclization being complete, the crude product was worked up as described in Example 2. Yield: 82 parts of 2-amino-6-chlorobenzothiazole=88.8% of th.

EXAMPLE 4

186.5 Parts of 4-chlorophenylthiourea and 42 parts of magnesium carbonate were added with stirring to 1,000 parts of chlorotoluene, and the suspension was heated to about 50° C. At this temperature, 225 parts of sulfuryl chloride was added dropwise within 2 hours ½, the batch was stirred for a further 3 hours until the gas development had ceased. 200 Parts of water were then added, and the batch was adjusted to pH 8–8.5 by means of concentrated ammonia. After removal of the chlorotoluene by means of steam distillation, the 2-amino-6-chlorobenzothiazole was suction-filtered at room temperature, washed with water and dried. Yield: 167 parts=90.5% of th.

EXAMPLE 5

230 Parts of sulfuryl chloride were added uniformly within about 2 hours to a mixture of 221 parts of 3,4-dichlorophenylthiourea, 1,000 parts of o-dichlorobenzene and 25 parts of magnesium oxide. The gas development being terminated, the filter residue was introduced into 500 parts of water, and the adhering o-dichlorobenzene was blown off by steam. The pH was adjusted to 7–8 by adding about 85 parts of 25% aqueous ammonia, and the precipitated mixture of 2-amino-5,6- and 6,7-dichlorobenzothiazole was isolated by filtration. After drying, 205 parts of final product having an isomer ratio of 6:4 and a melting point of 180°–198° C. (93.7% of th.) were obtained.

EXAMPLE 6

Operations were as described in Example 5 with the difference that the magnesium oxide was replaced by an equivalent amount of potassium carbonate. A similar result was obtained.

EXAMPLE 7

210 Parts of sulfuryl chloride were added within about 2 hours at a temperature of 35°–40° C. to a stirred mixture of 186.5 parts of 2-chlorophenylthiourea, 500 parts of toluene, 300 parts of chlorobenzene and 11 parts of sodium carbonate. The gas development being terminated, 250 parts of water were added, the solvent mixture was distilled off with steam, and the remaining aqueous phase was combined with 500 parts of 30% hydrochloric acid. Filtration from the undissolved matter was carried out at about 90° C., the filtrate was cooled to about 20° C., and the free amine was precipitated from the 2-amino-4-chlorobenzothiazole dissolved as hydrochloride by adding excess sodium hydroxide solution until a final pH of 8.5–9.0 was adjusted. The product was suction-filtered, washed to neutral with water, and dried. 170 Parts of 2-amino-4-chlorobenzothiazole having a melting point of 199°–200° C. (92.4% of th.) were obtained.

EXAMPLES 8–12

According to the indications of Examples 1 to 7 to the following scheme

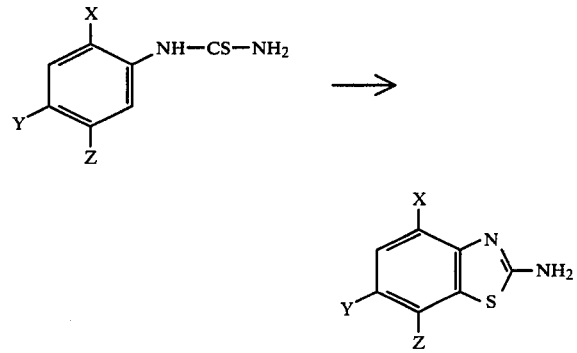

further phenylthioureas were cyclized to give 2-aminobenzothiazoles. The compounds obtained are listed in the following Table with respect to the position of substituents, yield and melting point:

| Example | X | Y | Z | Yield | Melting point |
| --- | --- | --- | --- | --- | --- |
| 8 | H | Br | H | 92.5% | 210–212° C. |
| 9 | Cl | Cl | H | 94.0% | 248–251° C. |
| 10 | Br | Br | H | 89.2% | 227–231° C. |
| 11 | Cl | Cl | Cl | 87.9% | 292–294° C. |
| 12 | Cl | H | Cl | 89.8% | 231–234° C. |

COMPARATIVE EXAMPLE 1

186.5 parts of 4-chlorophenylthiourea were suspended with stirring in 850 parts of chlorobenzene, and 185 parts of sulfuryl chloride were added uniformly with stirring at a temperature of 40°–45° C. within about 3 hours. After the immediately starting gas development had ceased, the suspension formed which could be stirred with difficulty only was liberated from the chlorobenzene by steam distillation. The remaining suspension of 2-amino-6-chlorobenzothiazolium chloride was adjusted to pH 8 with 25% ammonia solution, thus causing the crude 2-amino-6-chlorobenzothiazole to agglomerate to a tacky mass. By decantation and drying, 146.3 parts of 2-amino-6-chlorobenzothiazole containing about 85% of pure product were obtained (=124.4 parts of 100% product, 67.4% of th.).

Purification by redissolution or recrystallization was difficult and caused great losses. At best, 69.0 parts of 2-amino-6-chlorobenzothiazole containing >95% of pure product (37.4% of th.) were obtained from the crude product by repeated redissolution via the hydrochloride and adsorptive purification of the aqueous solution with active charcoal.

COMPARATIVE EXAMPLE 2

190 Parts of sulfuryl chloride added homogeneously within 4 hours at a temperature of 45°-50° C. with stirring to 231 parts of 4-bromophenylthiourea suspended in 1,200 parts of o-dichlorobenzene. After the gas development had ceased, the batch was cooled to about 20° C., the curde 2-amino-6-bromobenzothiazolium chloride precipitated was suction-filtered and washed with o-dichlorobenzene. The filter cake moist with the solvent was suspended in 1,000 parts of water, the adhering o-dichlorobenzene was distilled off by blowing in steam, and the solution of 2-amino-6-bromobenzothiazolium chloride obtained was filtered off from the greasy undissolved matter after having added 10 parts of active charcoal at 95° C. The clear filtrate was adjusted to pH 8 with 251/4% sodium hydroxide solution, which caused the free 2-amino-6-bromobenzothiazole to precipitate as yellowish, slightly tacky matter. After cooling, the solids having become vitreous were isolated and dried in vacuo at 40°-50° C. 167 Parts of 2-amino-6-bromobenzothiazole having a purity degree of 88% were obtained (=147.1 parts of 100% compound, 64.2% of th.). By repeated redissolution in dilute hydrochloric acid with addition of active charcoal, 2-amino-6-bromobenzothiazole having a purity degree of >95% was obtained. However, this purification was very expensive and caused great losses, so that at best 82 parts of the intended compound were obtained (35.8% of th., relative to 4-bromophenylthiourea used).

What is claimed is:

1. A process for the preparation of halogen-substituted 2-aminobenzothiazoles of the formula (1)

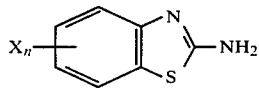

starting from halogen-substituted phenylthioureas of the formula (2)

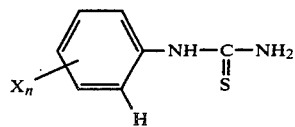

by cyclization reaction with sulfuryl chloride in an inert solvent, wherein X is chlorine, bromine or both chlorine and bromine and n is an integer of from 1 to 4, and the cyclization reaction is carried out in the presence of an alkali metal or alkaline earth metal oxide, hydroxide or carbonate.

2. The process as claimed in claim 1, wherein the cyclization reaction is carried out at a temperature in the range of about 30° C. to about 80° C., preferably about 45° C. to about 65° C.

3. The process as claimed in claim 1, wherein the cyclization reaction is carried out with addition of from 0.5 to 10 weight % of water, relative to the phenylthiourea used.

4. The process as claimed in claim 1, wherein from 1.1 to 2, preferably 1.3 to 1.7, mols of sulfuryl chloride per mol of phenylthiourea are used.

5. The process as claimed in claim 1, wherein the cyclization reaction is carried out in the presence of magnesium oxide and/or calcium oxide and/or barium oxide.

6. The process as claimed in claim 1, wherein the cyclization reaction is carried out in the presence of magnesium oxide.

7. The process as claimed in claim 1, wherein alkyl-substituted aromatic substances, haloaliphatic substances, and especially haloaromatic substances are used as solvent.

8. The process as claimed in claim 1, wherein a solvent or solvent mixture of solvents selected from the group of toluene, xylenes, ethylene chloride, trichloroethane, trichloroethylene is used.

9. The process as claimed in claim 1, wherein a solvent or solvent mixture of solvents selected from the group of chlorobenzene, bromobenzene, dichlorobenzenes, trichlorobenzenes, chlorotoluenes is used.

* * * * *